United States Patent [19]

Drauz et al.

[11] Patent Number: 5,543,397
[45] Date of Patent: Aug. 6, 1996

[54] NEW N-ACYL DIPEPTIDES AND THEIR USE

[75] Inventors: Karlheinz Drauz, Freigericht; Günter Knaup, Bruchköbel; Ulrich Groeger, Aschaffenburg, all of Germany

[73] Assignee: Degussa Aktiengesellschaft, Frankfurt am Main, Germany

[21] Appl. No.: 255,888

[22] Filed: Jun. 7, 1994

Related U.S. Application Data

[63] Continuation of Ser. No. 727,903, Jul. 10, 1991, abandoned.

[30] Foreign Application Priority Data

Jul. 12, 1990 [DE] Germany ............ 40 22 267.5

[51] Int. Cl.$^6$ ............................................. C07C 103/52
[52] U.S. Cl. ............................................. 514/19; 548/496
[58] Field of Search ........................... 548/496, 19

[56] References Cited

FOREIGN PATENT DOCUMENTS

| 0050196 | 4/1982 | European Pat. Off. . |
| 2071670 | 9/1981 | United Kingdom . |

OTHER PUBLICATIONS

Article entitled "Polymers Containing Enzymatically Degradable..." in Makromol, Chem. 182, 799–809 (1981).
Article entitled "Polymers Cont. Enzymatically Degrad. Bonds ..." in Makromol Chem. 182, 1899–1915 (1981).
Article entitiled "Reactive Copolymers of N–(2–Hydroxypropl) . . ." Makromol. Chem. 178, 2169–2183 (1977).
Article entitled "Acyl–peptide Hydrolase from Rat Liver" in the Journal of Biol. Chem. 1987 vol. 262, No. 24, Aug. 25, pp. 11435–11445, 1987 by Kazumi Kobayashi and John A. Smith.
Article entitled "Inhibition by Bestatin of a Mouse Ascites Tumor Dipeptidase" in the Journal of Biol. Chem. 1989 vol. 264, No. 14, Issue of May 15, pp. 8004–8011, 1989 by Elizabeth K. Patterson Chemical Abstracts vol. 85, 1976 p. 578.
Chemical Abstracts vol. 111, 1989, p. 23.
Chemical Abstracts vol. 107, 1987 p. 350.
Cas Registry Handbook p. 99976–95–1 258RO;Number section 1984–Supplement 1433RM.
Blodgett et al, "Direct Cleavage versus Transpeptidation in the Autodecomposition of Peptides Containing 2,4–Diaminobutanoic Acid (DABA) and 2,3–Diaminopropanoic Acid (DAPA) Residues. Specific Cleavage of DAPA–Containing Peptides", Journal of the American Chemical Society, Aug. 1989, pp. 6813–6821.
Kobayashi et al, "Acyl–peptide Hydrolase from Rat Liver: Characterization of Enzyme Reaction", Journal of Biological Chemistry, Aug. 1987, pp. 11435–11445.
Bizzozero et al, "Serine–Protease–Assisted Synthesis of Peptide Substrates for a α–Chymotrypsin", Helvetica Chimica Acta, Sep. 1982, pp. 1707–1719.
Chemical Abstracts, vol. 110, No. 5, Jan. 30, 1989.
Patent Abtracts of Japan, Nov. 26, 1990, re: JP–A–02 286 624.

*Primary Examiner*—David B. Springer
*Attorney, Agent, or Firm*—Cushman Darby & Cushman, L.L.P.

[57] ABSTRACT

Novel N-acyl depeptides of the formula:

$$R^2\text{—NH—CHR}^1\text{—CO—AS}$$

in which AS, $R^1$ and $R^2$ have certain, more precisely defined meanings. These N-acyl dipeptides are more stable under conditions of sterilization (121° C.) than corresponding, non-acylated dipeptides. On the other hand, they are cleaved more rapidly and more completely at the peptide bond in the living organism than the cleavage of the acyl group from simple N-acyl amino acids takes place. They can therefore be used with advantage as a source for the carbon terminal amino acid in mixtures and solutions for artificial nutrition or in culture media for cell cultures.

3 Claims, 1 Drawing Sheet

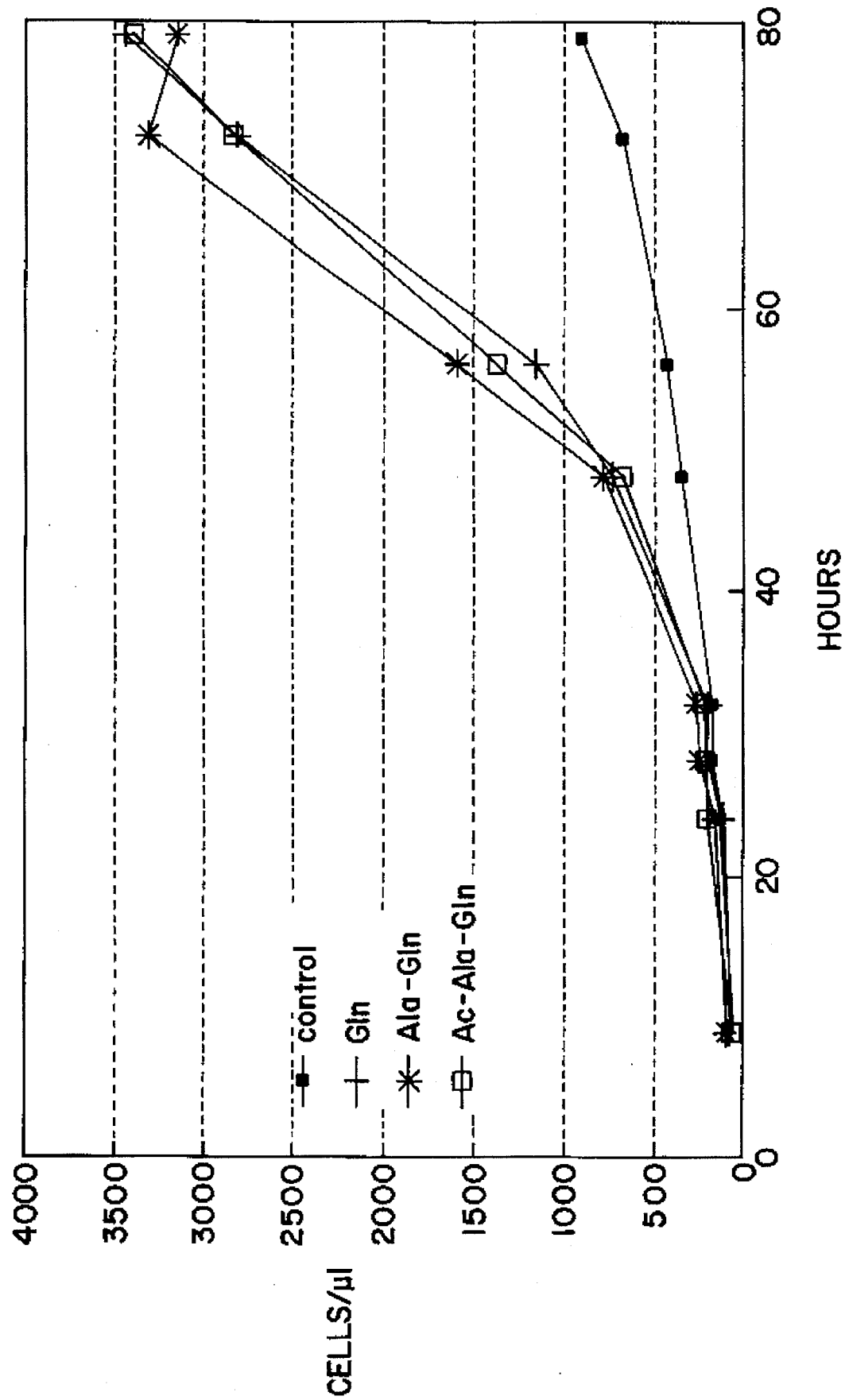

NEW N-ACYL DIPEPTIDES AND THEIR USE

This is a continuation of Applicaiton Ser. No. 07/727,903, filed on Jul. 10, 1991, now abandoned.

The present invention relates to novel N-acyl dipeptides of the formula:

$$R^2-NH-CHR^1-CO-AS \qquad (I)$$

In Formula I, AS stands for the residue obtained by removing a hydrogen from the nitrogen atom of an amino acid selected from the group consisting of isoleucine, tyrosine, glutamine and cysteine, when $R^1$ signifies hydrogen and $R^2$ a formyl group, or in which AS stands for the residue obtained by removing a hydrogen from the nitrogen atom of an amino acid selected from the group consisting of valine, isoleucine, tyrosine, Glutamine and cysteine, when $R^1$ signifies a methyl group and $R^2$ a formyl group, or in which AS stands for the residue obtained by removing a hydrogen from the nitrogen atom of an amino acid selected from the group consisting of isoleucine, glutamine and cysteine, when $R^1$ signifies hydrogen or a methyl group and $R^2$ an acetyl group, or in which AS stands for the residue obtained by removing a hydrogen from the nitrotten atom of an amino acid selected from the group consisting of valine, leucine, isoleucine, tyrosine, glutamine and cysteine when $R^1$ signifies hydrogen or a methyl group and $R^2$ an acyl group of an aliphatic mono-or dicarboxylic acid with 3 to 6 carbon atoms with the exception of methacrylic acid and when $R^1$ signifies a methyl group and AS stands for isoleucine, with the exception of 3-methyl butyric acid. The invention also relates to the pharmaceutically acceptable, physiologically compatible carboxylic-acid salts of these compounds.

BACKGROUND OF THE INVENTION

The use of dipeptides as source for certain amino acids as component of mixtures or solutions for artificial nutrition is known (see European patent EP-B-0 087 750, German patent DE-C-31 08 079 and European patent EP-A-0 182 356). The use of such dipeptides is especially appropriate if the free amino acids to be administered are poorly soluble in water, such as cystine, tyrosine, tryptophane, valine, leucine or isoleucine, or are not stable in aqueous solution, such as glutamine or cysteine.

The use of dipeptides of glutamine as a component of culture media for cell cultures is also known (see European patent EP-A-0 220 379).

Both infusion solutions and culture media for cell cultures must be used in a sterile form. The simplest and most commonly employed possibility for sterilization is the brief heating of the ready solutions to a temperature of 120° C. The known dipeptides can cyclo-condense to 2,5-diketopiperazines under these conditions, and this can occur even during a fairly long storage.

However, it is known that such 2,5-diketopiperazines exhibit a higher tendency to epimerize than the corresponding linear dipeptides (J. Am. Chem. Soc., vol. 108 (1986), pp. 7327–7332). The presence of the corresponding stereoisomeric 2,5-diketopiperazines must consequently always be considered and dealt with, when using dipeptide solutions, about whose physiological effects no experiments have been previously made in most instances.

It is also known that infusion solutions can use as source for certain amino acids the corresponding N-acetyl derivatives, which are, however, only utilized to an incomplete extent biologically. The cleavage both of N-acyl amino acids as well as of certain dipeptides takes place primarily in the kidneys (Metabolism, vol. 35 (1986), pp. 830–836; Z. Ern ährungswiss. 21 (1982), pp. 21–26). In addition, dipeptides are also cleaved in the blood plasma.

EP-A-0 267 179 suggested using corresponding N-acyl peptides, e.g. bis-(acetylglycyl)-L,L-cystine, in nutrient compounds as a replacement for the thermally unstable di-and tripeptides of cystine. However, experiments with rats have shown that bis-(acetylglycyl)-L,L-cystine is not suitable as a cysteine source in parenteral nutrition (Z. Ern ährungswiss. 28 (1989)., pp. 32–35).

SUMMARY OF THE INVENTION

It was surprisingly found that at least the C-terminal amino acid is split off in the living organism from certain N-acyl dipeptides in which the C-terminal amino acid is not cystine, so that they are suitable as source for this amino acid. In contrast to the free dipeptides, these N-acyl dipeptides are not already split in the blood plasma; however, a rapid splitting takes place in the kidney. It was possible to document this in an impressive manner by means of in vitro experiments with pig liver homogenizate. For example, N-acetyl-L-alanyl-m-tyrosine is cleaved 10 times more rapidly and N-butyyl-L-alanyl-L-tyrosine even 15 times more rapidly than N-acetlyl-L-tyrosine.

Furthermore, it was found that N-acyl dipeptides can be used as a source for the C-terminal amino acids in cell culture media. For example, the cell growth of L1210 mice leukemia cells shows no significant differences when the culture media was supplemented either with L-glutamine, L-alanyl-L-glutamine or N-acetyl-L-alanyl-L-glutamine. But in all three cases, the cell growth was increased drastically compared to a glutamine free media. The fact that N-acetyl-L-alanyl-L-glutamine is used by the cells as glutamine source is very surprising, since the related N-acetyl-Lglutamine is, if at all, only a very poor source.

Since these N-acyl dipeptides are, in addition, absolutely stable under the conventional conditions for heat sterilization (5 to 20 minutes at 121° C.), in contrast to the free dipeptides, they ARE advantageous as a source for the particular C-terminal amino acid which can not be directly used in infusion solutions and culture media for cell cultures as a consequence of its poor solubility or instability.

The invention also provides a solution or mixture for use as a nutrient or in a culture medium for cell cultures which comprises an N-acyl dipeptides of the formula $$R^2-NH-CHR^1-CO-AS \qquad (I'),$$

in which AS stands for the residue obtained by removing hydrogen from the nitrogen atom of an amino acid selected from the group consisting of valine, leucine, isoleucine, tyrosine, tryptophane, glutamine and cysteine, $R^1$ signifies the side chain of a natural amino acid and $R^2$ a formyl- or acetyl group or an acyl group of an aliphatic (alkyl or alkylene) mono- or dicarboxylic acid with 3 to 6 carbon atoms and their pharmaceutically acceptable physiologically compatible carboxylic-acid salts, the said dipeptides acting as a source for the C-terminal amino acid.

The N-acyl dipeptides of the invention or to be used in accordance with the invention can be present with free terminal carboxyl group or in the form of their physiologically compatible carboxylic-acid salts. Potential cations in such salts are e.g. alkali metals, alkaline-earth metals, cations of basic amino acids or cations of amines of the formula $NR^3R^4R^5$, in which $R^3$, $R^4$ and $R^5$ are identical or different and signify hydrogen, a $C_2$–$C_6$ hydroxyalkyl group or $C_1$–$C_6$ alkyl group, or two of the groups $R^3$, $R^4$ and $R^5$ are joined to form a heterocyclic ring which optionally also contains an oxygen atom or another nitrogen atom.

Preferred acyl groups $R^2$ in Formulas I and I' are the formyl-, acetyl-, propionyl-, butyryl-, succinyl- or hydroxysuccinyl group. As N-terminal amino acid, glycine ($R^1$=H) and alanine ($R^1$=CH$_3$) are preferred.

The N-acyl dipeptides of the invention or to be used in accordance with the invention can be produced in a simple manner in various ways. For example, the corresponding N-acyl amino acids can be coupled according to known methods of peptide chemistry, e.g. via active esters, mixed anhydrides or enzymatically with amino acids or C-terminal-protected amino acids (cf. Houben-Weyl, volume 15, "Synthese von Peptiden" Georg Thieme Verlag, Stuttgart, 1974).

Alternatively, free dipeptides which are present can be subsequently acylated with acyl halides or acyl anhydrides. The reaction with acyl halides or acyl anhydrides of an aliphatic carboxylic acid with 2 to 6 carbon atoms takes place under Schotten-Baumann conditions, preferably in water. If required by the solubility properties of the dipeptides and/or of the acylation reagent, mixtures of water and of an organic solvent miscible with water, e.g. a lower alcohol, acetone or tetrahydrofuran, can also be used as solvent. Sodium hydroxide is preferred as base for the acylation reaction. Aqueous, saline peptide solutions such as those which accumulate in some peptide syntheses, e.g. in the N-carboxylic-acid anhydride method, can also be used directly, if necessary, for acylation.

The production of the N-formyl dipeptides can take place in a manner analogous to the production of N-formyl amino acids by reacting the free dipeptides with the mixed anhydride from formic acid and acetic acid (cf. Houben-Weyl, vol. 15/1 "Synthese von Peptiden", Georg Thieme Verlag, Stuttgart, 1974, pp. 164 ff.).

In all instances, the N-acyl dipeptides can be liberated by acidifying with a mineral acid, at which time the N-acyl dipeptides, which are less soluble in water, precipitate directly. N-acyl dipeptides which are readily soluble in water can be extracted with an organic solvent immiscible with water. N-acyl dipeptides which are readily soluble in water can also be liberated by treatment with a strongly acidic ion exchanger in the H$^+$form and are then obtained in the form of an aqueous solution.

The carboxylic-acid salts of N-acyl dipeptides are produced by dissolving equimolar amounts of the N-acyl dipeptide and of the corresponding base in water. They can be obtained in solid form by means of concentrating the solution by evaporation or by means of precipitation with an organic solvent miscible with water; however, they are preferably used further directly in the form of the aqueous solutions obtained.

DETAILED DESCRIPTION OF PREFERRED EMBODIMENTS

The invention is illustrated in more detail in the following examples.

EXAMPLE 1

0.1 mole L-alanyl-L-tyrosine was dissolved in 50 ml 2N sodium hydroxide solution. 0.11 mole acetic anhydride were added drop-by-drop at 0° C. [in 18 ml tetrahydrofuran and 27.5 ml 4N sodium hydroxide solution] in such a manner that the pH of the reaction mixture was constantly at approximately 11. After the end of the addition, the mixture was agitated for 1 hour, then acidified with concentrated hydrochloric acid to pH 1 and the volume of the solution concentrated by one-half by evaporation. The N-acetyl-L-alanyl-L-tyrosine crystallized out, was filtered off, washed with water and dried.

Yield: 11.08 g (38 % of theory)

Melting point: 206° C.

1H-NMR (DMSO-d6): 1.17 (d, 3H), 1.83 (s, 3H), 2.87(dd. 2H), 4.30(m, 2H), 6.63(d, 2H), 6.98(d, 2H) 7.94(d, 1H), 7.96(d, 2H) 9.19(br.s, 1H), 12 . 60 (br. s, 1H)

The cleavage of the N-acetyl-L-alanyl-L-tyrosine by means of pig-kidney homogenizate was examined as follows:

140 g freshly slaughtered pig kidneys were cut into small pieces and homogenized with 200 ml ice-cold physiological solution of sodium chloride. 1 ml of the supernatant obtained after 30 minutes centrifugation at 10,000 rpms was mixed with 1 ml 0.1M tris/HCl (pH 7) buffer and 1 ml of a 30 mM solution of the substrate in 0.1M tris/HCl (pH 7) buffer and incubated at 37° C. The decrease in time of the substrate concentration was followed by HPLC.

The specific activity of the kidney homogenizate determined in this manner related to N-acetyl-L-alanyl-L-tyrosine was 420 nmoles per minute and g kidney.

Related to a specimen of N-acetyl-L-tyrosine examined in the same manner for the sake of comparison, the kidney homogenizate exhibited a specific activity of 43 nmoles per minute and g kidney.

EXAMPLE 2

0.12 mole butyryl chloride and 0.12 mole 4N sodium hydroxide solution were added drop-by-drop to 0.1 mole L-alanyl-L-tyrosine in 50 ml 2N sodium hydroxide solution in such a manner that the pH of the reaction mixture was constantly between 10 and 11. After termination of the addition, the mixture was acidified with concentrated hydrochloric acid to pH 1 and extracted with ethyl acetate. The extract was evaporated to dryness under reduced pressure. The yield of N-butyryl-L-alanyl-L-tyrosine was 18.37 g (47% of theory).

Melting point: 27°–28° C.

$^1$H-NMR (DMSO-d6): 0.83(t,3H), 1.17(d,3H), 1.50(m, 2H) 2.08(t, 2H), 2.80(m, 1H), 2.92(m, 1H) 4.34(m, 2H), 6.65(d, 2H), 6.99( d, 2H) 7.87(m, 2H), 9.18(br. s, 1H), 12.50(br.s,1H)

In the experiment described in Example 1, the kidney homogenizate exhibited a specific activity of 660 nmoles per minute and g kidney related to N-butyryl-L-alanyl-L-tyrosine.

EXAMPLE 3

The same method was used as in Example 1 with the single difference that instead of L-alanyl-L-tyrosine, 0.1 mole L-alanyl-L-glutamine was used. The yield of N-acetyl-L-alanyl-L-glutamine was 13.44 g (52% of theory).

Melting point: 160° C.

$^1$H-NMR (DMSO-d6): 1.18(d,3H), 1.81(s,3H 1.70–2.05(m, 2H), 2.13(m,2H), 4.18(m, 1H), 4.32 (m, 1H), 6.78(br.s,1H), 7.29(br.s,1H), 8.05(d, 1H), 8.16(d, 1H), 12.55(br. s, 1H)

The suitability of N-acetyl-L-alanyl-L-glutamine as glutamine source in cell culture media was determined by the following experiment:

6 ml of a suspension of L1210 mice leukemia cells (50 cells/µl) was, after washing two times with PBS, incubated in T25 culture flasks at 37° C., 10% $CO_2$ and 90% humidity in a medium composed of 20 ml RPMI 1640+herpes 25 mmolar (Boehringer Mannhelm), 5 ml FCS active (Seromed), 0.09 ml mercaptoethanol 1: 1000 (Merck), 0.25 ml penicillin streptomycin (Gibco) and 0.25 ml of a 0.2 molar solution of either L-glutamine, L-alanyl-L-glutamine or N-acetyl-L-alanyl-L-glutamine. The cell numbers were determined in a counting chamber. The results are shown in FIG. 1.

EXAMPLE 4

The same method was used as in Example 1 with the single difference that, instead of L-alanyl-L-tyrosine, 0.1 mole L-alanyl-L-valine was used. The yield of N-acetyl-L-alanyl-L-valine was 17.72 g (77% of theory).

Melting point: 147° C.

$^1$H-NMR (DMSO-$d_6$): 0.94(d,6H), 1.28(d,3H), 1.92(s, 3H) 2.16(m, 1H), 4.23(dd, 1H), 4.49(dq, 1H) 7.96(d, 1H), 8.11(d, 1H), 12.65(br, s. 1H)

EXAMPLE 5

0.1 mole L-alanyl-L-leucine was acylated as in Example 1. The N-acetyl-L-alanyl-L-leucine crystallized out immediately upon acidification of the reaction mixture. The yield was 17.8 g (73% of theory).

Melting point: 145° C.

$^1$H-NMR (DMSO-d6): 0.84(d,3H), 0.90(d,3H), 1.18(d, 3H), 1.62(m, 2H), 1.61(m, 1H), 1.82(s,3H), 4.20(m, 1H), 4.31(m, 1H), 7.97(d, 1H), 8.00(d, 1H), 12.48(br.s,1H)

EXAMPLE 6

The same method was used as in Example 1 with the single difference that instead of L-alanyl-L-tyrosine, 0.1 mole L-alanyl-L-isoleucine was used. The yield of N-acetyl-L-alanyl-L-isoleucine was 19.44 g (80% of theory).

Melting point: 124° C.

$^1$H-NMR (DMSO-$d_6$): 0.87(d,3H), 0.87(t,3H), 1.18(d, 3H), 1.18(m, 1H), 1.41(m, 1H), 1.79(m, 1H) 1.82(s, 3H), 4.18(dd, 1H), 4.39(dq, 1H), 7.88(d, 1H), 8.00(d, 1H) 12.54(br. s, 1H)

EXAMPLE 7

0.05 mole L-alanyl-L-tryptophane was dissolved in 25 ml 2N sodium hydroxide solution. 0.055 mole acetic anhydride was added drop-by-drop at 0° C. into 9 ml tetrahydrofuran and 13.7 ml 4N sodium hydroxide solution in such a manner that the pH of the reaction mixture was constantly at approximately 11. After the end of the addition, the mixture was agitated 1 hour, then acidified with concentrated hydrochloric acid to pH 1. The N-acetyl-L-alanyl-L-tryptophane crystallized out, was filtered off, washed with water and dried. The yield was 14.74 g (93% of theory).

Melting point: 214° C. (with decomposition)

$^1$H-NMR (DMSO-$d_6$): 1.18(d,3H), 1.79(s,3H), 3.12(m, 2H) 4.46(m, 1H), 7.00(m,2H) 4.32(dq, 1H), 7.16(s,1H), 7.33(d, 1H), 7.51(d, 1H) 7.95(d, 1H), 7.99(d, 1H) 10.87(br.s, 1H), 12.62(br. s, 1H)

EXAMPLE 8

The same method was used as in Example 1 with the single difference that, instead of L-alanyl-L-tyrosine, 0.1 mole glycyl-L-valine was used. The yield of N-acetyl-glycyl-L-valine was 10.69 g (50% of theory).

Melting point: 133° C.

$^1$H-NMR ($D_2O$): 0.82(d,3H), 0.87(d, 3H), 1.95(s,3H) 2.08(m, 1H), 3.86(s,2H), 4.18(d, 1H)

EXAMPLE 9

The same method was used as in Example 1 with the single difference that instead of L-alanyl-L-tyrosine, 0.1 mole glycyl-L-leucine was used. The yield of N-acetyl-glycyl-L-leucine was 3.33 g (15% of theory).

Melting point: 125° C.

$^1$H-NMR (DMSO-d6): 0.79(d,3H), 0.84(d,3H), 1.47(m, 2H), 1.56(m, 1H), 1.80(s, 3H), 3.66(d,2H), 4.19(m, 1H), 8.02(m, 2H) 12.50(br. s, 1H)

EXAMPLE 10

The same method was used as in Example 1 with the single difference that instead of L-alanyl-L-tyrosine, 0.1 mole glycyl-L-tyrosine was used. The yield of N-acetyl-glycyl-L-tyrosine was 20.2 g (72% of theory).

Melting point: 162° C.

$^1$H-NMR (DMSO-$d_6$): 1.83(s,3H), 2.78(dd, 1H), 2.92(dd, 1H), 3.68(m, 2H), 4.37(m, 1H), 6.67(d, 2H), 6.99(d,2H), 7.98(d, 1H) 8.02(d, 1H), 9.20(br.s, 1H), 12.66(br.s,1H)

EXAMPLE 11

The same method was used as in Example 1 with the single difference that instead of L-alanyl-L-tyrosine, 0.1 mole glycyl-L-glutamine was used. The yield of N-acetyl-glycyl-L-glutamine was 23.70 g (96% of theory).

Melting point: 193° C. (under decomposition)

$^1$H-NMR ($D_2O$): 1.90(m, 1H), 2.02(s,3H), 2.10(m, 1H) 2.27(t,2H), 3.81(s,2H), 4.32(dd, 1H)

EXAMPLE 12

70 ml acetic anhydride were added drop-by-drop to a solution of 0.1 mole L-alanyl-L-tyrosine in 200 ml formic acid with cooling in such a manner that the temperature remained between 5 and 1° C. The mixture was then stirred for 2 hours without cooling. Then, 80 ml ice water were added. The reaction mixture was evaporated to dryness and the residue recrystallized from water. The yield of N-formyl-L-alanyl-L-tyrosine was 17.46 g (62% of theory).

Melting point: 163° C.

$^1$H-NMR (DMSO-d6): 1.17(d,3H), 2.86(m, 2H), 4.46(m, 2H), 6.63(d,2H), 6.99(d,2H), 7.96(s,1H) 8.08(d,1H), 8.18(d, 1H)

EXAMPLE 13

The same method was used as in Example 12 with the single difference that instead of L-alanyl-L-tyrosine, 0.1 mole L-alanyl-L-glutamine was used. The residue remaining after the concentration by evaporation was recrystallized from water/ethanol. The yield of N-formyl-L-alanyl-L-glutamine was 9.32 g (38% of theory).

Melting point: 150° C.

¹H-NMR (DMSO-d6): 1.21(d,3H), 1.79(m, 1H), 1.96(m, 1H), 2.13(m, 2H), 4.12(m, 1H), 4.41(dq, 1H), 6.77(br. s, 1H), 7.27(br. s, 1H), 8.22(d,2H), 12.30(br.s,1H)

EXAMPLE 14

The same method was used as in Example 12 with the single difference that instead of L-alanyl-L-tyrosine, 0.1 mole glycyl-L-tyrosine was used. The residue remaining after the concentration by evaporation was recrystallized from water/ethanol. The yield of N-formyl-glycyl-L-tyrosine was 5.50 g (21% of theory).

Melting point: 182° C.

¹H-NMR (DMSO-d6): 2.83(m,2H), 3.77(m, 2H), 4.37(m, 1H), 6.64(d,2H), 6.98(d,2H), 8.03(s,1H), 8.13(m, 2H)

EXAMPLE 15

35 ml acetic anhydride were added drop-by-drop to a solution of 0.05 mole glycyl-L-glutamine in 100 ml formic acid with cooling in such a manner that the temperature remained between 5 and 15° C. The mixture was then stirred for 2 hours without cooling. Then, 40 ml ice water were added. The reaction mixture was evaporated to dryness and the residue recrystallized from methanol/isopropanol. The yield of N-formyl-glycyl-L-glutamine was 6.57 g (29% of theory).

Melting point: 168° C. (with decomposition)

¹H-NMR (DMSO-d6): 1.79(m, 1H), 1.98(m, 1H), 2.10(m, 2H) 3.79(m,2H), 4.18(m, 1H), 6.77(br.s, 1H), 7.28(br.s, 1H), 8.05(s,1H), 8.20(m, 2H)

EXAMPLE 16

0.1 mole L-alanyl-L-glutamine was dissolved in 50 ml 2N sodium hydroxide solution. 0.11 mole propionic acid anhydride were added drop-by-drop at 0° C. [in 18 ml tetrahydrofuran and 27.5 ml 4N sodium hydroxide solution] in such a manner that the pH of the reaction mixture was constantly at approximately 11. After the end of the addition, the mixture was agitated for 1 hour, then acidified with concentrated hydrochloric acid to pH 1 and the volume of the solution concentrated by one half by evaporation. The N-propionyl-L-alanyl-L-glutamine crystallized out, was filtered off, washed with water and dried.

Yield: 19.41 g (71% of theory)

Melting point: 78°–82° C.

¹H-NMR (D₂O): 0.98(t,3H), 1.28(d,3H), 1.89(m, 1H), 2.10(m, 1H), 2.15(m, 2H), 2.24(q,2H), 4.17(q, 1H), 4.27(dd, 1H)

EXAMPLE 17

The same method was used as in Example 16 with the single difference that instead of L-alanyl-L-glutamine, 0.1 mole L-alanyl-L-tyrosine was used. The yield of N-propionyl-L-alanyl-L-tyrosine was 17.28 g (56% of theory).

Melting point: 64° C.

¹H-NM$_R$ (DMSO-d6): 0.98(t,3H), 1.18(d,3H), 2.10(q, 2H), 2.87(m, 2H), 4.32(m,2H), 6.67(d,2H), 7.01(d,2H), 7.90(m, 2H)

EXAMPLE 18

The same method was used as in Example 16 with the single difference that instead of L-alanyl-L-glutamine, 0.1 mole glycyl-L-glutamine was used. The yield of N-propionyl-glycyl-L-glutamine was 21.49 g (83% of theory).

Melting point: 130° C.

¹H-NMR (D₂O): 1.12(t,3H), 2.02(m, 1H), 2.24(m, 1H), 2.37(m,4H), 3.95(s,2H), 4.41(m, 1H)

EXAMPLE 19

0.06 mole butyryl chloride and 0.06 mole 4N sodium hydroxide solution were added drop-by-drop to 0.05 mole L-alanyl--leucine in 25 ml 2N sodium hydroxide solution in such a manner that the pH of the reaction mixture was constantly between 10 and 11. After termination of the addition, the mixture was acidified with concentrated hydrochloric acid to pH 1 and extracted with ethyl acetate. The extract was evaporated to dryness under reduced pressure. The yield of N-butyryl-L-alanyl-L-leucine was 7.07 g (50% of theory).

Melting point: 155° C.

¹H-NMR (DMSO-d6): 0.90(m, 9H), 1.18(d,3H), 1.50(m, 4H), 1.62(m, 1H), 2.09(t,2H), 4.23(m, 1H), 4.37(m, 1H), 7.92(d, 1H), 7.99(d, 1H), 12.50(hr. s, 1H)

EXAMPLE 20

The same method was used as in Example 19 with the single difference that instead of butyryl chloride, 0.06 mole hexanoyl chloride was used. The yield of N-hexanoyl-L-alanyl-L-leucine was 8.77 g (58% of theory).

Melting point: 112° C.

¹H-NMR (DMSO-d6): 0.90(m, 9H), 1.18(d,3H), 1.24(m, 4H), 1.52(m, 4H), 1.62(m, 1H), 2.10(t,2H), 4.21(m, 1H), 4.36(m, 1H), 7.91(d, 1H), 7.96(d, 1H), 12.60(br.s,1H)

EXAMPLE 21

20 mmoles succinic acid anhydride were added to a solution of 10 mmoles L-alanyl-L-isoleucine, 10 mmoles sodium hydroxide and 25 mmoles sodium bicarbonate in 60 ml water. The reaction mixture was agitated 15 hours at room temperature and then acidified with concentrated hydrochloric acid to pH 2. The reaction mixture was evaporated to dryness under reduced pressure and the residue extracted with 40 ml isopropanol. The N-succinyl-L-alanyl-L-isoleucine was precipitated from the extract by means of the addition of ether.

Yield: 1.32 g (43% of theory)

Melting point: 118°–120° C.

¹H-NMR (DMSO-d6): 0.88(m, 6H), 1.16(m, 1H), 1.18(d, 3H), 1.38(m, 1H), 1.68(m, 1H), 2.42(m, 4H), 4.38(m, 1H), 7.85(d, 1H), 8.02(d, 1H), 12.20(br. s, 1H)

EXAMPLE 22

The same method was used as in Example 21 with the single difference that instead of L-alanyl-L-isoleucine, 10 moles L-alanyl-L-glutamine were used. The yield of N-succinyl-L-alanyl-L-glutamine was 2.27 g (76% of theory).

Melting point: 106°–108° C.

¹H-NMR (D₂O):1.19(d,3H), 1.80(m, 1H), 1.98(m, 1H), 2.17(m, 2H), 2.42(m, 4H), 4.13(m, 2H)

EXAMPLE 23

The same method was used as in Example 21 with the single difference that instead of L-alanyl-L-isoleucine, 10 moles glycyl-L-glutamine was used. The yield of N-succinyl-glycyl-L-glutamine was 2.23 g (82% of theory).

Melting point: 98°–100° C.

$^1$H-NMR (DMSO-d$_6$): 1.78(m, 1H), 1.95(m, 1H), 2.16(m, 2H), 2.46(m, 4H), 3.76(m, 2H), 4.18(m, 1H), 8.12(d, 1H), 8.20(m, 1H), 10.60(br.s,2H)

EXAMPLE 24

16 mmoles succinic acid anhydride were added to a solution of 8 moles L-alanyl-L-tyrosine, 8 moles sodium hydroxide and 20 mmoles sodium bicarbonate in 50 ml water. The reaction mixture was agitated 15 hours at room temperature and then acidified with concentrated hydrochloric acid to pH 2. The reaction mixture was evaporated to dryness under reduced pressure and the residue extracted with 50 ml isopropanol. The isopropanol was evaporated under reduced pressure and 1.32 g (50% of theory) N-succinyl-L-alanyl-L-tyrosine remained in the form of a viscous oil.

$^1$H-NMR (D$_2$O): 1.20(d,3H), 2.49(m, 2H), 2.62(m, 2H), 3.05(m, 1H), 3.22(m, 1H), 4.24(q, 1H), 4.63(m, 1H), 7.03(d, 2H), 7.30(d, 2H)

EXAMPLE 25

0.055 mole L-leucyl-L-glutamine was dissolved in 27.5 ml 2 N sodium hydroxide solution. 0.060 mole acetic anhydride and 15 ml 4 N sodium hydroxide solution were added drop-by-drop in such a manner that the pH of the reaction mixture was constantly higher than 10. After the end of the addition, the mixture was agitated for 1 hour, then demineralized by chromatography on an acidic ion exchange resin. The eluate was concentrated under reduced pressure until crystallization began, then 40 ml acetone was added and the N-acetyl-L-leucyl-L-glutamine was filtered off.

Yield: 6.6 g (42% of theory).

$^1$H-NMR (DMSO-d6): 0.88(d,3H), 0.91(d,3H), 1.42(m, 2H), 1.63(m, 1H), 1.80(m, 1H), 1.85(s, 3H), 1.94(m, 1H), 2.13(m, 2H), 4.13(m, 1H), 4.33(m, 1H), 6.76(br.s,1H), 7.24(br.s,1H), 7.92(d, 1H), 8.18(d, 1H), 12.48(br.s,1H)

What is claimed is:

1. A composition suitable for use as a glutamine source in a culture medium, comprising an N-acyl dipeptide of the formula:

$$R^2-NH-CHR^1-CO-AS \qquad (I')$$

in which AS stands for the residue obtained by removing a hydrogen from the nitrogen atom of an amino acid selected from the group consisting of valine, leucine, isoleucine, tryosine, tryptophan, glutamine and cysteine, when $R^1$ signifies the side chain of a natural amino acid and $R^2$ a formyl- or acetyl group or an acyl group of an aliphatic mono- or dicarboxylic acid containing 3 to 6 carbon atoms, and their physiologically compatible carboxylic-acid salts as a source for said amino acid.

2. A culture medium as set forth in claim 1 in which the N-acyl dipeptide is N-acetyl-L-alanyl-L-glutamine.

3. The composition according to claim 1, wherein said culture medium is a tissue cell culture medium.

* * * * *